United States Patent [19]

McLaughlin et al.

[11] Patent Number: 5,308,242
[45] Date of Patent: May 3, 1994

[54] DISPOSABLE HANDPIECE FOR DENTAL PROCEDURES

[76] Inventors: Roger McLaughlin; Delwin K. McCarthy; Clyde Barson, all of 40485-D Murrieta Hot Sp. Rd., Murrieta, Calif. 92563

[21] Appl. No.: 889,072

[22] Filed: May 26, 1992

[51] Int. Cl.$^5$ .......................... A61C 1/10; A61C 3/00; A61C 1/08; A61C 1/14
[52] U.S. Cl. ................................. 433/114; 433/126; 433/127
[58] Field of Search ............... 433/114, 125, 126, 127, 433/132

[56] References Cited

U.S. PATENT DOCUMENTS

| | | | |
|---|---|---|---|
| 3,946,490 | 3/1976 | Sotman et al. | 433/132 |
| 3,955,284 | 5/1976 | Balson | 433/132 |
| 4,406,470 | 9/1983 | Kataoka et al. | 279/1 SG |
| 4,661,060 | 4/1987 | Strohmaier | 433/82 |
| 4,795,343 | 1/1989 | Choisser | 433/116 |
| 4,842,516 | 6/1989 | Choisser | 433/132 |
| 4,978,297 | 12/1990 | Vlock | 433/88 |
| 5,028,233 | 6/1991 | Witherby | 433/125 |
| 5,156,547 | 10/1992 | Bailey | 433/125 |
| 5,160,263 | 11/1992 | Meller et al. | 433/125 |

Primary Examiner—Gene Mancene
Assistant Examiner—Cindy A. Cherichetti

[57] ABSTRACT

A disposable hand tool of the compressed air drive type is disclosed for use in performing dental procedures on a workpiece. An elongated body has conduits penetrating a base at one end of the body. The conduits allow entry of a light beam, a pressurized water stream, and a compressed air stream into the body. The base includes attachment threads for securing the body to a source of the light beam, pressurized water stream, and compressed air stream. A plurality of passageways are in communication with the conduits for conducting the light beam, the water stream, and the air stream through the body. A head at the opposite end of the body contains bearings attached to a supporting shaft. The shaft includes a turbine impeller and a clamping hole for removable attachment of a dental bur to the shaft. The air stream drives the impeller at a high speed for rotating the bur about a rotational axis. An opening in the body adjacent to the head allows release of the light beam, the pressurized water stream, and a portion of the compressed air stream in a direction toward the distal end of the bur so that the bur, the light beam, the water stream, and the air stream may all converge on the workpiece.

7 Claims, 3 Drawing Sheets

5,308,242

DISPOSABLE HANDPIECE FOR DENTAL PROCEDURES

FIELD OF THE INVENTION

This invention relates generally to dental hand tools, and, more particularly, is directed toward a disposable dental hand tool.

BACKGROUND OF THE INVENTION

It is well known that infectious agents such as viruses and bacteria can be transmitted from one person to another through re-use of incompletely sterilized medical instruments, such as dental hand tools, syringes, and the like. As it is difficult to completely sterilize complex tools, such as air-driven dental hand tools, an effort has been made to make available disposable dental hand tools that are to be used with only one patient and then discarded. It is argued that such hand tools, if made of inexpensive plastic and not designed for an extended life, would become practical and inexpensive enough for use in many common dental procedures.

For example, U.S. Pat. No. 3,955,284 to Balson on May 11, 1976, discloses a disposable dental drill assembly. The advantages of such a disposable drill assembly, as disclosed, are based on economics, as opposed to patient and practitioner safety, and are motivated by the relatively high cost of purchasing a plurality of expensive, machined, extended-life hand tools. It is argued that such a disposable dental assembly, while not as durable as an expensive machined dental drill assembly, is more economical due to its inexpensive manufacturing cost. No mention is made, however, of using one such disposable drill assembly per patient to avoid infection.

As the concern over infectious disease has become more prominent, and injection molding techniques have become more refined and less expensive, other disposable dental hand tools have become available. U.S. Pat. Nos. 4,795,343 and 4,842,516, both to Choisser on Jan. 3, 1989 and Jun. 27, 1989, respectively, are examples of such disposable hand tools meant for use on a single patient specifically to reduce the risk of spreading disease. While such devices can be manufactured relatively inexpensively, such devices are also quite limited in their functionality.

For example, dental burs or diamond cutting tools of such devices are permanently mounted to a drive turbine, necessitating the use of as many such devices as dental burs are required for a particular patient. As a single dental procedure may easily require five or more different types of dental burs, such as drill bits of varying sizes and shapes, polishers, prophylactic angles, and the like, a practitioner may have to use five or more such disposable hand tools for a single patient, subsequently discarding all of them.

Moreover, such devices are limited to supplying an air stream for driving a turbine attached to the bur. Frequently, however, it is necessary to flush the work site with air and water. Consequently, using such devices requires additional water and air supplying implements, and causes further congestion in the already crowded working environment of a person's mouth. Further, the means by which rotation is imparted to the turbines of such devices provides less torque than many conventional hand tools.

A further drawback of such disposable devices is evident in that it is often difficult to properly illuminate a person's mouth when a number of implements are inserted in the mouth. Yet such disposable dental hand tools provide no means of illuminating the work site. Consequently, while devices of this type do help reduce the risk of spreading diseases between patients, the lack of functionality inherent in such devices requires additional expense, equipment, and time on the part of the dental practitioner and, therefore, the patient.

Clearly, a disposable dental hand tool is needed that overcomes the drawbacks of those devices found in the prior art. Such a needed device would be inexpensive to manufacture, thereby making it practical to dispose of after use with one patient. Moreover, such a needed device would allow the replacement of different dental burs, making it unnecessary to use more than one such device for each patient. Further, such a needed device would allow the insertion of burs of various sizes and shapes, and would make removal and insertion of such burs easy to accomplish without significantly increasing the size of the device. Still further, such a needed device would provide means of delivering water, air, and light to the work site. Such a needed device would additionally provide a high degree of torque and control to the dental bur, making it easy for the dental practitioner to use. Still further, such a needed device would be light weight, easy to grasp and manipulate, and easy to connect to a standard source of air, water, and light. The present invention fulfills these needs and provides further related advantages.

SUMMARY OF THE INVENTION

The present invention is a disposable hand tool of the compressed air drive type for use in performing dental procedures on a workpiece, such as a tooth or filling. An elongated body has conduits penetrating a base at one end of the body. The conduits allow entry of a light beam, a pressurized water stream, and a compressed air stream into the body. The base includes attachment means for securing the body to a source of the light beam, pressurized water stream, and compressed air stream. A plurality of passageways are in communication with the conduits for conducting the light beam, the water stream, and the air stream through the body. The body includes a pair of shell halves and a core. The shell halves are joined to define a cavity within, and can be easily formed with conventional injection molding techniques. The cavity wall comprises a first set of integrally formed groves, and the core provides a second set of integrally formed groves for mating with the first set of grooves. When mated, the first set and the second set of integrally formed grooves are matched in shape such that the enclosed passageways are thereby formed along the longitudinal axis of the body.

A head at the other end of the body contains bearings attached to a supporting shaft. The shaft includes a turbine impeller and a removable attachment means for attachment of a dental bur to the shaft. The air stream drives the impeller at a high speed for rotating the bur about a rotational axis.

An opening in the body adjacent to the head allows release of the light beam, the pressurized water stream, and a portion of the compressed air stream in a direction toward the distal end of the bur so that the bur, the light beam, the water stream, and the air stream all converge on the workpiece to enable illumination, cooling and removal of debris from the workpiece during the dental procedures. Preferably, one passageway contains a transparent, light conducting rod for conducting the light beam efficiently from the base to the opening. A major portion of the air stream is directed to the turbine impeller, and a minor portion of the air stream is diverted to move through one of the passageways, through the opening, and toward the workpiece.

The present invention is inexpensive to manufacture, thereby making it practical to dispose of after use with one patient. As such, the present invention accomplishes the objective of considerably reducing the risk of spreading disease between patients. Further, the present invention facilitates quick and easy replacement of various sizes and shapes of dental burs, making it unnecessary to use more than one of the present invention with each patient. Further, the present invention allows the quick exchange of dental burs without significantly increasing the size of the device. Still further, the present invention provides a means of delivering water, air, and light to the work site in a single dental instrument. The present invention additionally provides a high degree of torque and control to the dental bur, making it easy and comfortable for the dental practitioner to use. Still further, the present device is light weight, easy to grasp and manipulate, and quickly connects to a standard source of air, water, and light. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
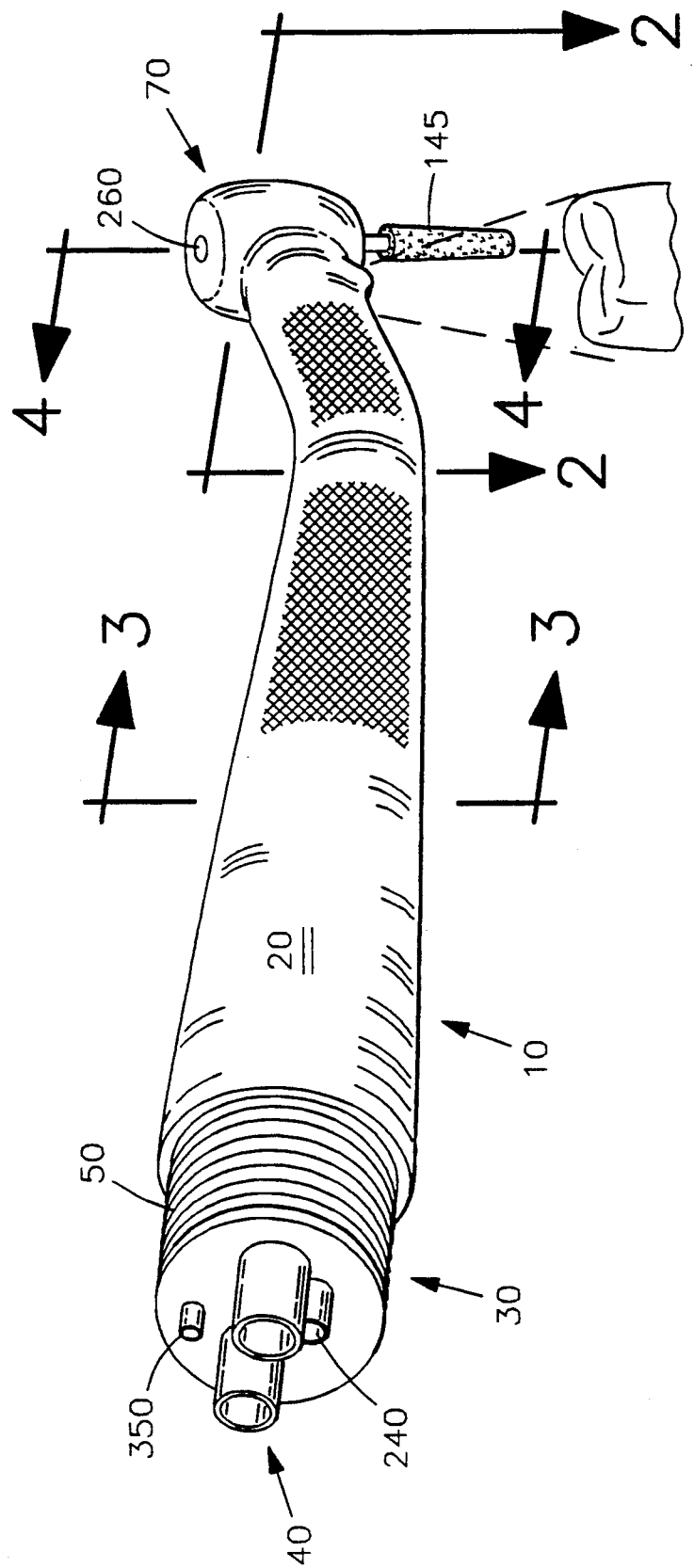
FIG. 1 is a perspective illustration of the present invention, illustrating conduits in a base at one end of a body of the invention, and further illustrating a dental bur and a workpiece.
Figure 5:
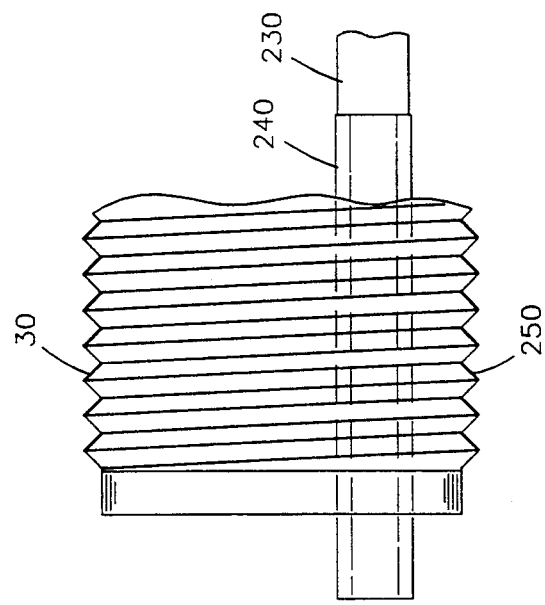
FIG. 5 is a partial elevational view of the invention, illustrating the base of the invention with an external thread and a light conducting rod stub.

FIG. 1 shows a disposable hand tool of the compressed air drive type for use in performing dental procedures on a workpiece, such as a tooth or filling. A portable, elongated body 10 has an exterior surface 20, which may have a variety of different textures suited for allowing firm grasping and manipulation of the body 10. Conduits 40 penetrate a base 30 of the body 10 at one end of the body 10 and allow entry of a light beam 41, a pressurized water stream 42, and a compressed air stream 43 into the body 10. Conduits 40 further provide an exit from the body 10 of a return air stream (FIG. 1). The base 30 further includes attachment means 50 for securing the body 10 to a source (not shown) of the light beam 41, pressurized water stream, and compressed air stream 43. Preferably the attachment means 50 is an external thread formed integrally on the base 30 (FIG. 5), for mating with an internal thread on the source (not shown). A plurality of internal passageways 160 are in communication with the conduits 40 for conducting the light beam 41, the water stream, and the air stream 43 through the body 10. Preferably, the present invention is made entirely of a relatively inexpensive material, such as plastic, whereby the invention is inexpensive enough to be disposed of after use, or given to a patient perhaps to be used at a later date.

Figure 3B:
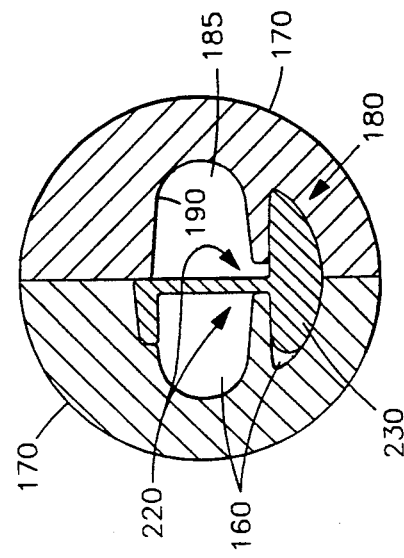
FIG. 3B is a cross sectional view of the invention, taken generally along lines 3—3 of FIG. 1, and illustrating the two shell halves of FIG. 3A and a core of the invention.
Figure 3A:
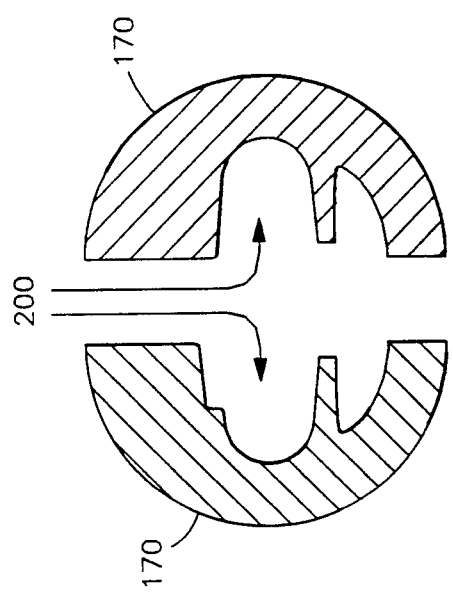
FIG. 3A is a partial and exploded cross sectional view of the invention, taken generally along lines 3—3 of FIG. 1, and illustrating two shell halves of the body of the invention.

Preferably, the body 10 is constructed as a pair of shell halves 170 (FIGS. 3A and 3B) and a core 180. The shell halves 170 are joined to establish the exterior surface 20 of the body 10 and to define a cavity 185 within, and can be easily formed with conventional injection molding techniques. The cavity wall 190 comprises a first set 200 of integrally formed groves aligned generally with the longitudinal axis of the body 10. The core 180 provides a second set 220 of integrally formed groves for mating with the first set 200 of grooves (FIG. 3B). When mated, the first set 200 and the second set 220 of integrally formed grooves are matched in shape such that the enclosed passageways 160 are thereby formed primarily along the longitudinal axis of the body 10. In one embodiment of the invention, one of the conduits 40, designated as the tubular conduit 350 for carrying the water stream 42, is positioned to penetrate the base 30 at a position generally above the core 180. The water stream 42 is then directed from the conduit 350 laterally around the core 180 to reach a position generally lateral to the core, thereafter moving longitudinally adjacent to the under surface of the core 180 to reach the opening 150 for ejection of the water stream 42.

Figure 4:
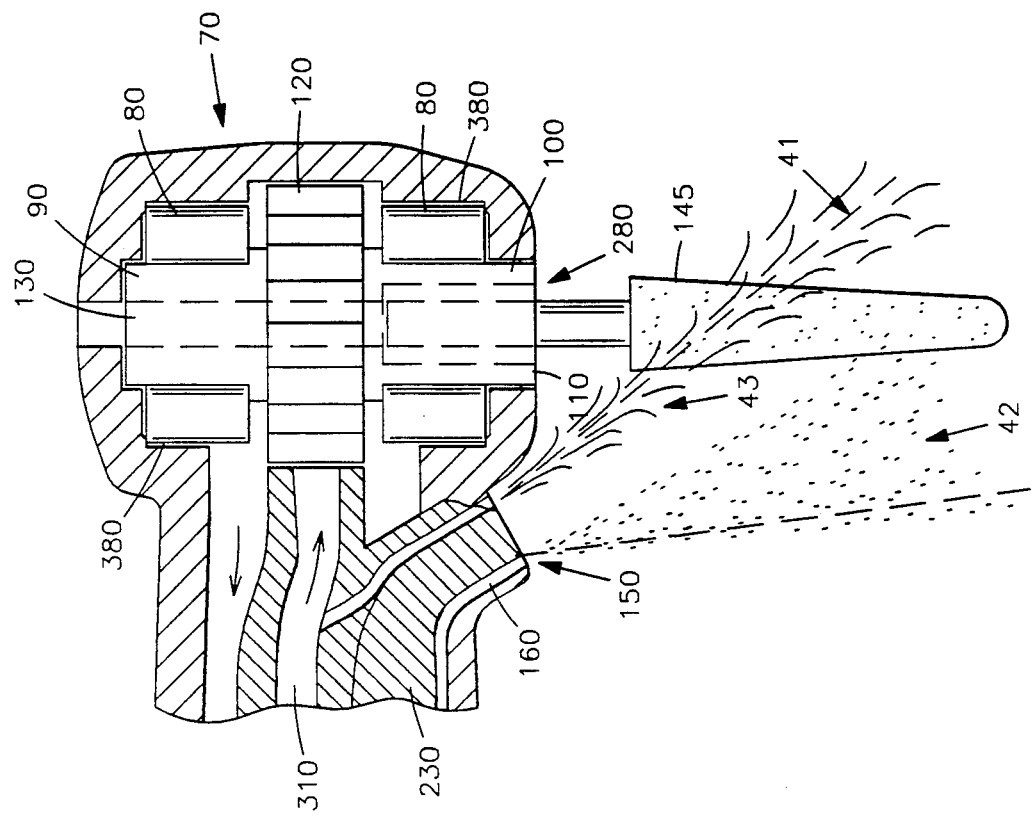
FIG. 4 is a cross sectional view of the invention, taken generally along lines 4—4 of FIG. 1, and illustrating bearings, a supporting shaft, and an opening of the invention.

A head 70 at the other end of the body 10 contains bearings 80 attached to an upper portion 90 and a lower portion 100 of a supporting shaft 110 (FIG. 4). The shaft 110 includes a turbine impeller 120 and a bur removal means 130, preferably a through hole for inserting a removal tool to poke a dental bur 145 out of the shaft 110. The air stream 43 drives the impeller 120 at a high speed for rotating the bur 145 about a rotational axis. The dental bur 145 is supported by a clamping means 280 in a downwardly projecting direction from the head 70. The dental bur 145 includes a bur mounting shaft, and may be any of a number of different dental tools such as a drill bit, a prophylactic cup, a polisher, a diamond cutting tool, or the like.

The head 70 further includes a pair of bearing mounting cavities 380 for accepting the outer races of the bearings 80 (FIG. 4). As the disposable dental tool of the present invention does not require long-term functional reliability, the bearings 80 may be conventional, metallic bearings, or, alternatively, may be formed from less expensive, non-metallic materials such as hard plastic. The cavities 380 are formed so as to urge the outer races of the bearings 80 toward each other to achieve a predetermined amount of preload. As such, the shaft 110 is confined to rotational motion only, with lateral motion of the shaft 110 being significantly limited.

Figure 6:
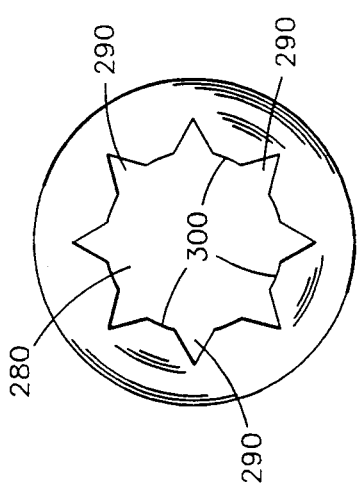
FIG. 6 a partial plan view of the invention, illustrating a clamping hole and relief cutouts of a supporting shaft of the invention.

In the preferred embodiment of the invention, the clamping means 280 of the support shaft 110 is a clamping hole that is aligned with the rotational axis of the shaft 110. The clamping hole has a smaller diameter than that of the bur mounting shaft, whereby the clamping hole provides an interference fit to the bur mounting shaft. The clamping hole has preferably a series of relief cutouts 290 on the sidewall 300 of the clamping hole to permit the sidewall 300 to be forced open to accommodate the bur mounting shaft. As the shaft 110 is made from a resilient material, the bur 145 may be inserted into the clamping hole to be held tightly in place by the sidewall 300 (FIG. 6). The head 70 further includes an access hole 260 aligned approximately with the rotational axis of the shaft 110 and the bur removal means 130, whereby the bur 145 may be disengaged from the shaft 110 (FIGS. 1 and 4) so as to insert a new bur 145, for example. The elasticity of the shaft 110 provides for self-center and allows repeated disengagement and insertion of the bur 145.

An opening 150 in the body 10 adjacent to the head 70 allows release of the light beam 41, the pressurized water stream 42, and a portion of the compressed air stream 43 in a direction toward the distal end of the bur 145 so that the bur 145, the light beam 41, the water stream 42, and the air stream 43 all converge on the workpiece to enable illumination, cooling and removal of debris from the workpiece during the dental procedure. Light conducting rod 230 partly fills opening 150, leaving small apertures 151 at either side of rod 230 for disbursing water 42 and air 43 streams. Preferably, one of the passageways 160 contains a transparent, light conducting rod 230 having a highly polished surface for conducting the light beam 41 efficiently from the base 30 to the opening 150. Likewise, one of the tubular conduits 40 preferably contains a highly polished light conducting rod stub 240 (FIG. 5) for efficiently conducting the light beam 41 through the base 30 from the source of the light (not shown) to the light conducting rod 230. In one embodiment of the invention, the water stream 42 is released adjacent to the light conducting rod 230 at the opening 150 such that the rod 230 forms one side of the passage 160 that carries the water stream 42. Likewise, the light rod 230 may form one side of the passage 310 to accommodate the air stream 43.

Figure 2:
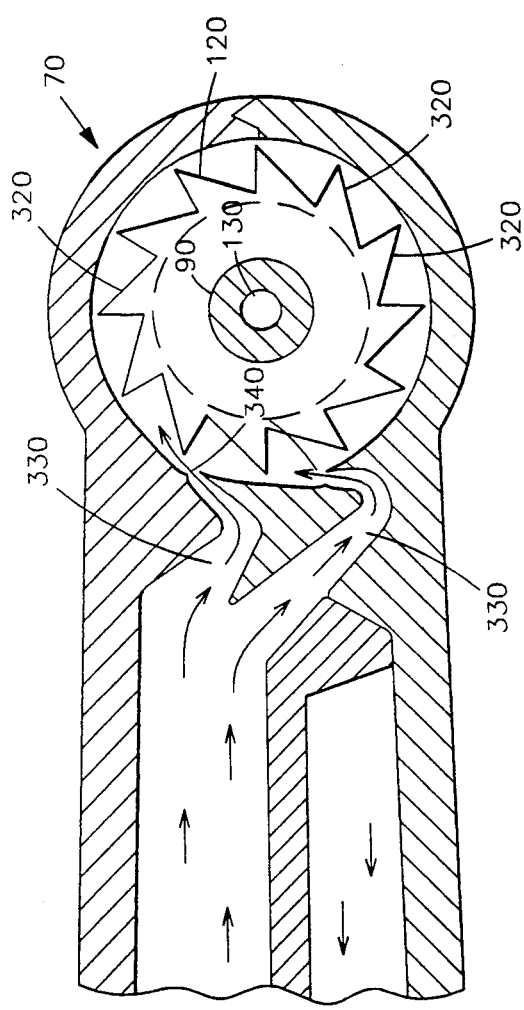
FIG. 2 is a partial cross sectional view of the invention, taken generally along lines 2—2 of FIG. 1, and illustrating air passageways and an impeller of a head of the invention.

Referring now to FIGS. 2 and 4, a major portion of the air stream 43 is directed to the turbine impeller 120. The impeller 120 has a plurality of blades 320 for receiving the stream of air. The stream of air is directed against the impeller blades 320 through two separate passages 330, each of which are shaped as a nozzle 340 for effectively projecting the major portion of the air stream 43 against the blades 320. The nozzles 340 are each positioned relative to the impeller 120 so that at least one of the blades 320 receives a portion of the air stream 43 primarily orthogonally to the surface of at least one of the blades 320 at each rotational position of the impeller 120 (FIG. 2), thereby providing a consistent high rotational torque force on the dental tool. Meanwhile, a minor portion of the air stream 43 is diverted to move through one of the passageways 310 (FIG. 4) to one of the apertures 151 adjacent to the light conducting rod 230 such that this minor portion of the air stream 43 is directed toward the workpiece to remove debris from the workpiece.

In operation, a dental practitioner selects an appropriate bur 145 for the required dental procedure and inserts the bur mounting shaft of the bur 145 into the clamping hole of the shaft 110. The sidewall 300 of clamping hole flexes to allow insertion of the bur mounting shaft, at least some of the sidewall 300 material is displaced into relief cutouts 290 (FIG. 6). The dental practitioner then uses the attachment means 50 of the body 10 to connect the base 30 of the body 10 to a source of pressurized water, pressurized air, and light. During a typical dental procedure, the dental practitioner activates the pressurized air and light together at the source, and activate the pressurized water with a foot pedal or other actuator for cooling the workpiece and flushing away debris.

When he activates the pressurized water source, such as through a foot pedal or other control means on the source (not shown), water is forced through the conduit 350 of the base 30 at a position above the core 180, then laterally around the core 180 to reach a position lateral to the core 180, and then through one passageway 160 toward the head 70. The stream of water then exits through an opening 150 in a direction toward the distal end of the bur 145, so as to flush away debris and apply water to the workpiece for cooling.

When the light source is activated, light travels through the light conducting rod stub 240 through the base 30 to the light conducting rod 230, where it is passed through the opening 150 toward the workpiece, thereby illuminating the workpiece.

When the pressurized air source is activated, the air stream 43 flows through a conduit 40, through a passageway 160, and is divided into a major and minor portion. The major portion is then passed through two separate passages 330, each that end at an air nozzle 340 for directing the air stream 43 against the blades 320 of the impeller 120. The force of the air against the blades 320 causes the impeller 120 to rotate, thereby driving the bur 145. The air then leaves the head 70 through at least one return air passage (FIGS. 2 and 4). The minor portion of the air stream 43 is diverted to move through one passageway 310, through one of the apertures 151, and toward the workpiece, so as to blow away debris from the workpiece and dry the workpiece.

Once the dental procedure requiring the bur 145 has been completed, the dental practitioner then pokes an elongated object through the access hole 260 of the head 70 to remove the bur 145 from the clamping hole. A new bur 145 may be inserted, or, if all procedures are complete, the disposable hand tool of the present invention may be discarded.

While the invention has been described with reference to a preferred embodiment, it is to be clearly understood by those skilled in the art that the invention is not limited thereto. Rather, the scope of the invention is to be interpreted only in conjunction with the appended claims.

I claim:

1. A disposable hand tool of the compressed air drive type for use in performing dental procedures on a workpiece, the tool comprising:
    an elongated body including a pair of shell halves and a core, the shell halves being joined to establish an exterior surface for manual grasping and manipulation of the body, and further, forming a cavity within, the cavity wall comprising a first set of integrally formed grooves aligned with the longitudinal axis of the body, the core providing a second set of integrally formed grooves for mating with the first set of grooves, the first and the second sets of grooves being matched in shape and location so as to define a set of longitudinal passageways as enclosed fluid conduits in the body;

a base at one end of the body in which a plurality of tubular conduits penetrate for conducting entry into the body of a light beam, a pressurized water stream and a compressed air stream and for providing an exit from the body of the air stream, the base having means for attachment of the body to a source of the light beam, pressurized water stream and compressed air stream, the tubular conduits mating with the enclosed conduits within the body; and a head at the other end of the body in which bearings are attached to the upper and lower portions of a supporting shaft provided with a turbine impeller, and a means for removable attachment of a dental bur supported in a downwardly projecting direction, the air stream driving the impeller at high speed for rotating the bur about a rotational axis;

an opening in the body adjacent the head for release of the light beam the pressurized water stream and a portion of the compressed air stream in a direction approximating the projecting direction of the bur so that the bur, the light beam, the water and the air stream all converge on the workpiece to enable illumination, cooling and removal of debris from the workpiece during said procedures.

2. A disposable hand tool of the compressed air drive type for use in performing dental procedures on a workpiece in accordance with claim 1 wherein the head has an access hole aligned approximately with the rotational axis of the shaft in order to enable an elongated object to be inserted into the access hole to poke the bur out of the shaft for dismounting the bur from the removable mounting means of the shaft.

3. A disposable hand tool of the compressed air drive type for use in performing dental procedures on a workpiece in accordance with claim 1 wherein the bur, having a bur mounting shaft for attaching the bur to the supporting shaft, the attachment means is a clamping hole, said hole aligned with the rotational axis of the supporting shaft for accepting the bur mounting shaft, the clamping hole having a diameter smaller than the diameter of the bur mounting shaft so that the clamping hole provides an interference fit to the bur mounting shaft, the clamping hole having at least one relief cutout on the sidewall of the clamping hole to permit the clamping hole to be forced open to accommodate the bur mounting shaft whereby the bur is tightly held in place by the sidewall of the hole and is aligned with the centerline of the hole.

4. A disposable hand tool of the compressed air drive type for use in performing dental procedures on a workpiece in accordance with claim 1 wherein the water stream is released adjacent to the light conducting rod at the opening, the rod forming one side of the passage carrying said water stream.

5. A disposable hand tool of the compressed air drive type for use in performing dental procedures on a workpiece in accordance with claim 1 wherein a major portion of the air stream is directed to the impeller while a minor portion of the air stream is diverted to move through one of the passageways, to reach the opening adjacent the light conducting rod for ejection thereby, the rod forming one side of said passage carrying the air stream.

6. A disposable hand tool of the compressed air drive type for use in performing dental procedures on a workpiece in accordance with claim 1 wherein the head includes a pair of bearing mounting cavities for positioning the outer races of the bearings, the cavities being formed so as to urge the outer bearing races toward each other to achieve a predetermined amount of preload so that play in a dental tool is reduced.

7. A disposable hand tool of the compressed air drive type for use in performing dental procedures on a workpiece in accordance with claim 1 wherein the impeller has a plurality of blades for receiving the stream of air, each of the blades having a pointed linear edge separating a leading surface and a trailing surface, the stream being directed against the trailing surface through two separate air passages, each of the air passages being shaped to provide a converging nozzle for increasing the velocity of the air stream therethrough against each of the trailing surfaces in turn as the impeller rotates, the nozzles being positioned relative to the impeller so that when one of the trailing surfaces, is positioned to receive one portion of the air stream from one of the converging nozzles most efficiently, another of the trailing surfaces is positioned to receive another portion of the air stream from the other of the converging nozzles least efficiently, this relationship between the two nozzles reversing in recurring cycles in order to maintain a constant average force on the impeller, the pointed linear edge of each blade preventing the occurrence of a reversing force of the air stream against the leading surface of each blade.

* * * * *